United States Patent
Coppo

(10) Patent No.: US 6,306,977 B1
(45) Date of Patent: Oct. 23, 2001

(54) MERCAPTOALKYLAMIDE-FUNCTIONALIZED RESINS

(75) Inventor: Frank Teen Coppo, Lincoln University, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/255,902

(22) Filed: Feb. 23, 1999

Related U.S. Application Data

(60) Provisional application No. 60/076,529, filed on Mar. 2, 1998.

(51) Int. Cl.[7] .................................................. C08F 8/36
(52) U.S. Cl. .................................... 525/332.2; 525/328.9; 525/328.5; 525/333.5; 525/343; 525/374
(58) Field of Search ............................. 525/332.7, 328.3, 525/328.5

(56) References Cited

U.S. PATENT DOCUMENTS 5,478,893 12/1995 Ghosh ............................... 525/329.4

OTHER PUBLICATIONS

Rapp Polymere Gmbh, *Pricelist/Orderlist*, 1997, 24.
S.–H. L. Chiu, L. Anderson, "Oligosaccharide Synthesis . . . ", *Carbohydrate Research* 1976, 50, 227–238.
J. M. J. Fréchet et al., "Application of Phase–Transfer Catalysis . . . ", *J. Org. Chem.* 1979, 44, 1774–1778.
Th. J. Nieustad et al., "Reversible binding of sulfur dioxide . . . ", *Rec. trav. chim.* 1976, 95, 225–231.
S. Kobayashi et al., "Polymer–Supported . . . ", *Tetrahedron Lett.* 1996, 37, 2809–2812.
J. M J. Fréchet et al., "Functionalization of crosslinked . . . ", *Polymer* 1979, 20, 675–680.
C. R. Moore et al., "Proteolytic fragments . . . ", *Biochemistry*, 1989, 28, 9184–9191.
B. A. Burdick et al., "Polymeric thiols as enzymes activators . . . ", *Appl. Biochem. Biotechnol.*, 1987, 16, 145–156.
L. M. Gayo and M. J. Suto, "Traceless Linker . . . ", *Tetrahedron Lett.*, 1997, 38, 211–214.
J. Cerny and O. Wichterle, "Polythiouroniumverbingungen", *J. Polymer Sci.* 1958, 30, 501.
R. J. Booth and J. C. Hodges, "Polymer–Supported Quenching . . . ", *J. Am. Chem. Soc.* 1997, 119, 4882–4886.
M. W. Criswell et al., "Combinatorial Synthesis . . . ", *Tetrahedron* 1998, 54, 3983–3998.
J. R. Booth and J. C. Hodges, "Solid–Supported Reagent . . . ", *Acc. Chem. Res.* 1999, 32, 18–26.
S. W. Kaldor et al., "Use of Solid–Supported Nucleophiles . . . ", *Tetrahedron Lett.*, 1996, 37, 7193–7196.

*Primary Examiner*—Bernard Lipman

(57) ABSTRACT

Disclosed are polymers comprising mercaptoalkylamide-functionalized styrene units of Formula I

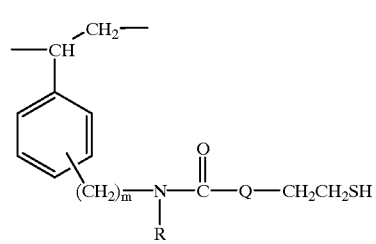

wherein
  m is an integer from 1 to 3;
  R is H or $C_1$–$C_3$ alkyl; and
  Q is a bond, —$CH_2$—, —$CH_2CH_2$—, —$CH_2CH_2CH_2$— or

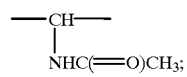

a process for their preparation, and their use as supports for solid phase synthesis of small molecules and as supported nucleophiles to aid solution phase synthesis.

20 Claims, No Drawings

MERCAPTOALKYLAMIDE-FUNCTIONALIZED RESINS

This application claims the priority benefit of U.S. Provisional Application 60/076,529, filed Mar. 2, 1998.

FIELD OF THE INVENTION

The present invention relates to a method of preparation of novel solid phase reagents useful as solid phase supports for small molecule synthesis, especially synthesis of heterocycles, and as supported nucleophiles to aid purification of solution phase reactions.

BACKGROUND OF THE INVENTION

The advent of combinatorial chemistry has sparked renewed interest in the use of functionalized polymers in the synthesis of small, organic molecules (for recent reviews, see Blackburn et al. "Functionalized Resins and Linkers for Solid-Phase Synthesis of Small Molecules", *Drugs of the Future* 1997, 22(9), 1007–1025; and Shuttleworth et al., "Functionalized Polymers: Recent Developments and New Applications in Synthetic Organic Chemistry", *Synthesis* 1997, 1217–1239). Inexpensive, readily prepared functionalized resins suitable for organic synthesis applications are increasingly needed.

Some thiol-functionalized polystyrene resins are known in the art. Literature methods for preparing thiomethyl-functionalized polystyrene resins involve multiple steps and give resins with low active SH titers unless significant care is taken to remove oxygen from all solvents and equipment (see J. Cerny and Wichterle, *J. Polymer Sci.* 1958, 30, 501, J. M. J. Frechet et al., *Polymer* 1979, 20, 675, and S. Kobayashi et al., *Tetrahedron Lett.* 1996, 37, 2809). Commercially available thiol-functionalized resins are expensive, have low loading and generally need pretreatment before use to remove a thiol protecting group.

Thiol-functionalized resins have found use as a solid phase support for the synthesis of substituted heterocycles (see Gayo and Suto, *Tetrahedron Lett.* 1997, 38, 211–214) and as supported nucleophiles to aid the purification of solution phase reactions involving excess electrophiles (Hodges, 2nd *Winter Conference on Medicinal and Bioorganic Chemistry*, Steamboat Springs, Colo., Jan. 26–31, 1997).

SUMMARY OF THE INVENTION

This invention pertains to a polymer comprising mercaptoalkylamide-functionalized styrene units of Formula I

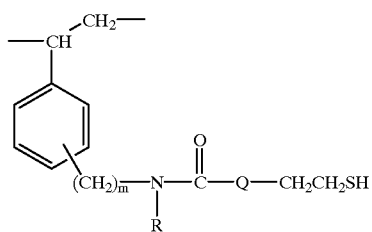

wherein
   m is an integer from 1 to 3;
   R is H or $C_1$–$C_3$ alkyl; and
   Q is a bond, —$CH_2$—, —$CH_2CH_2$—, —$CH_2CH_2CH_2$— or

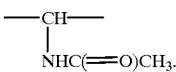

Said polymer is optionally grafted onto other polymers, such as polyethylene and polypropylene.

This invention also relates to beads of aforesaid polymer comprising mercaptoalkylamide-functionalized styrene units of Formula I.

Another aspect of this invention pertains to a process for preparing aforesaid polymer comprising mercaptoalkylamide-functionalized styrene units of Formula I, the process comprising the sequential steps of:

(a) contacting a polymer comprising aminoalkyl-functionalized styrene units of Formula II

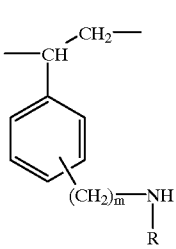

with a solvent to swell said polymer; and (b) reacting said polymer with a thiolactone of Formula III

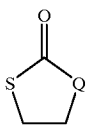

at temperature of 0 to 120° C.;
wherein m, R, and Q are as previously described.

Another aspect of this invention pertains to a method of using aforesaid polymer comprising mercaptoalkylamide-functionalized styrene units of Formula I as a support for solid phase synthesis of small molecules and as a supported nucleophile to aid solution phase synthesis.

DETAILS OF THE INVENTION

Mercaptoalkylamide-functionalized polystyrene resins with high active SH titers and a simple, single-step method to prepare these resins have now been discovered. The resins are useful as solid phase supports for small molecule synthesis, especially synthesis of heterocycles, and as supported nucleophiles to aid purification of solution phase reactions.

Resin is defined variously in the polymer arts (see M. S. M. Alger, *Polymer Science Dictionary*, Elsevier, N.Y., 1989, p. 415). In this disclosure, resin is synonymous with polymer. Styrene polymer, polymer comprising styrene units, polystyrene, polystyrene resin and styrene polymer resin are all synonymous. Functionalized styrene polymer, polymer comprising functionalized styrene units, functionalized polystyrene, functionalized polystyrene resin and functionalized styrene polymer resin are synonymous and refer to a composition of matter comprising polymer chains formed from units corresponding to a functionalized styrene monomer and optionally also other units corresponding to other monomers such as unfunctionalized styrene. As functionalized polystyrene is often made from unfunctionalized polystyrene and in the functionalization process not every unit is functionalized, functionalized polystyrene typically will comprise unfunctionalized as well as functionalized units. Functionalized polystyrene made from a mixture of functionalized and unfunctionalized styrene monomers will also comprise both functionalized and unfunctionalized units (for a description of copolymerization of chloromethylstyrene with a variety of other monomers, see J.-P. Montheard, M. Chatzopolous and M. Camps, "Functional Polymers via Free-Radical Polymerization of Chloromethylstyrene", in *Desk Reference of Functional Polymers, Syntheses and Applications,* R. Arshady, Ed., American Chemical Society, Washington, D.C. 1996, Chapter 1.1). In a mercaptoalkylamide-functionalized polystyrene of this invention, the unit corresponding to the functionalized styrene monomer is of Formula I as defined in the Summary of the Invention.

Preferred for reason of ease of synthesis or cost is a polymer comprising mercaptoalkylamide-functionalized styrene units of Formula I wherein m is 1. More preferred for reason of ease of synthesis or cost is said polymer wherein Q is —CH$_2$— or —CH(NHC(=O)CH$_3$)—. —CH(NHC(=O)CH$_3$)— means

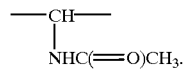

More preferred for reason of ease of synthesis or cost is said polymer wherein R is H. Most preferred for reason of highest titer of thiol per weight of polymer is said polymer wherein Q is —CH$_2$—.

The polymer chains in a mercaptoalkylamide-functionalized polystyrene of this invention preferably also comprise about 0.5 to about 20% by weight units corresponding to the divinylbenzene monomer to provide cross-linking so as to improve the physical strength and resistance to solvents of the derived resin. About 0.8 to 8% by weight divinylbenzene units is preferred. Most preferred is about 1 to 2% by weight divinylbenzene units, which provides resins with very good physical properties. The polystyrene chains optionally also comprise units derived from vinylethylbenzene and other substituted vinyl benzenes (as described for ion exchange resins by F. W. Billmeyer, Jr., *Textbook of Polymer Science,* Second Edition, Wiley-Interscience, New York, 1971, p. 407). Furthermore the polystyrene chains are optionally grafted onto other carbonaceous polymeric backbones such as polyethylene, polypropylene or fluoropolymers, as is well known in the art.

For reason of cost and obtaining greatest titer per weight of polymer, a preferred mercaptoalkylamide-functionalized polystyrene resin of the invention is not grafted onto other carbonaceous polymeric backbones, but simply comprises polystyrene chains cross-linked with units derived from divinylbenzene as described and wherein at least 1%, preferably at least 10%, of the styrene units are of Formula I and the remainder of the styrene units are unfunctionalized. Said preferred resin is referred to as consisting essentially of a polystyrene backbone.

A mercaptoalkylamide-functionalized styrene polymer of the invention is usually prepared and used in the form of small microporous or macroporous beads, having average particle diameters typically ranging from about 50 to about 500 μm, although larger or smaller sizes are possible. Functionalized styrene polymers serving as precursors are commercially available in the form of such beads, conveniently prepared by suspension polymerization (see E. C. Blossey and W. T. Ford, "Polymeric Reagents" in *Comprehensive Polymer Chemistry,* Vol. 6, G. Allen et al. Ed., Pergamon Press, New York, 1989, pp. 81–114, F. W. Billmeyer, Jr., *Textbook of Polymer Science,* Second Edition, Wiley-Interscience, New York, 1971, pp. 358–359, 407).

The mercaptoalkylamide-functionalized polystyrene resins of the invention comprise units of Formula I, which are prepared from corresponding units of Formula II according to the method outlined in Scheme 1 where m, R and Q are as previously defined.

Scheme 1

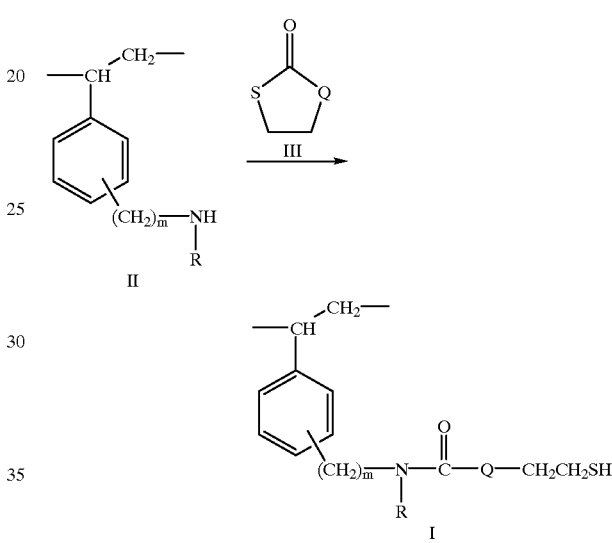

An amino-functionalized styrene polymer resin comprising units of Formula II is mixed with 1 to 10 equivalents of a thiolactone of Formula III in the presence of a solvent which promotes swelling of the resin, such as dichloromethane, tetrahydrofuran, dioxane or toluene, as known to one skilled in the art. The mixture is agitated for 1 to 96 hours at 0 to 120° C., returned to ambient temperature and filtered to collect the resin. The wet resin is thoroughly washed with fresh solvents by repeated resuspension and filtering techniques known to one skilled in the art and dried in vacuo to provide a mercaptoalkylamide-functionalized styrene polymer resin comprising units of Formula I.

Amino-functionalized styrene polymers are known in the art (see, for example, Merrifield et al., *Tetrahedron Lett.* 1976, 42, 3795–3798; and Mathur et al. *Polymers as Aids in Organic Synthesis,* Academic Press, New York, 1980) and many are commercially available (for example, 1% cross-linked aminomethylated poly(styrene-co-divinylbenzene) is available from suppliers such as Aldrich Chemical Company, aminomethylated polystyrene grafted polyethylene SynPhase™ crowns are available from Chiron Technologies and aminomethylated polystyrene grafted polypropylene MicroTube™ reactors are available from Irori Quantum Microchemistry). Thiolactones of Formula III are either commercially available or readily prepared by known methods (see Bhar and Chandrasekaran, *Tetrahedron* 1997, 53, 11835–11842).

The quality of the mercaptoalkylamide-functionalized resins prepared by the above method can be determined by elemental analysis of a suitable derivative as shown in Scheme 2. For example, 1% cross-linked mercaptobutyramidomethyl-functionalized poly(styrene-co-divinylberizene) (a styrene polymer comprising units of Formula I where m is 1, R is H, Q is CH$_2$) (Resin 1) is treated with excess 4-bromobenzyl bromide in the presence of N,N-diisopropylethylamine to give, after filtration, thorough washing and drying in vacuo, the derivatized Resin 2. The sulfur-to-bromine ratio, as determined by microanalysis, gives the loading level of the resin and allows one to calculate the number of equivalents of active SH groups per gram of Resin 1. Analysis by this method shows that resins such as Resin 1 have near theoretical levels of active SH groups and that only minor loss of active SH groups occur over storage in closed vessels at room temperature.

Scheme 2

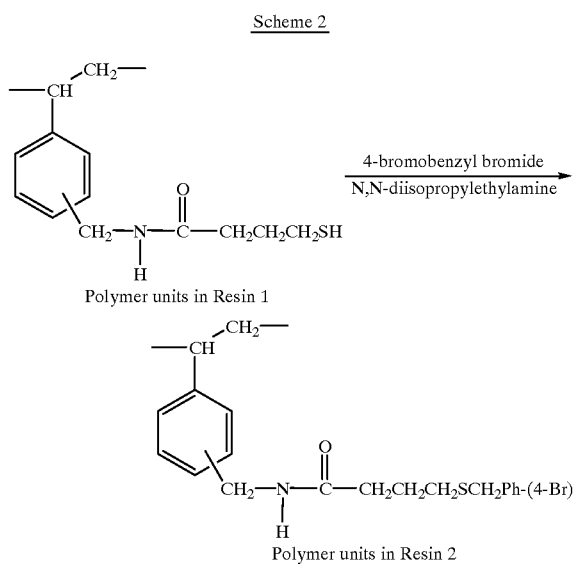

The mercaptoalkylamide-functionalized resins of the invention are useful as solid supports to aid organic synthetic methods. They are especially useful in facilitating combinatorial, parallel, and high-throughput automated synthesis of compound libraries via both solid phase and solution phase approaches.

In accordance with this invention a product compound may be produced from a modifiable substrate precursor that bonds to the sulfur atom of a mercaptan group using a method which comprises (a) reacting the precursor with a polymer comprising mercaptoalkylamide-functionalized styrene units of Formula I to bind the precursor to the sulfur of one of said functionalized styrene units, (b) modifying the bound precursor, (c) oxidizing the sulfur to which the modified precursor is bound, and (d) cleaving the modified precursor by nucleophilic displacement to produce the product compound, as outlined in Scheme 3.

Scheme 3

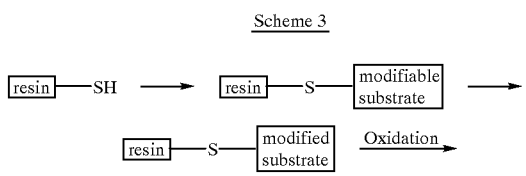

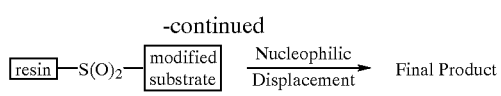

For example, 2-(3-trifluoromethylpyrazol-1-yl)-4-(3-trifluoromethylphenoxy)-5-methylpyrimidine (9) is prepared as shown in Scheme 4. Reaction of the aforementioned Resin 1 with 2,4-dichloro-5-methylpyrimidine (3) in the presence of N,N-diisopropylethyl-amine (DIEA) base in N,N-dimethylformamide (DMF) gives the pyrimidinyl bound resin 4. The reactive 2-chloro group is displaced by 3-trifluoromethylpyrazole (5) to give the resin-bound modified pyrimidine 6. Oxidation of the sulfur linkage using m-chloroperbenzoic acid (MCPBA) in ethyl acetate (EtOAc) to give the sulfone-linked resin 7 followed by displacement with 3-trifluoromethylphenol (8) in the presence of 1,8-diazabicyclo-[5.4.0]undec-7-ene (DBU) in a solvent such as dichloromethane completes the synthesis.

Scheme 4

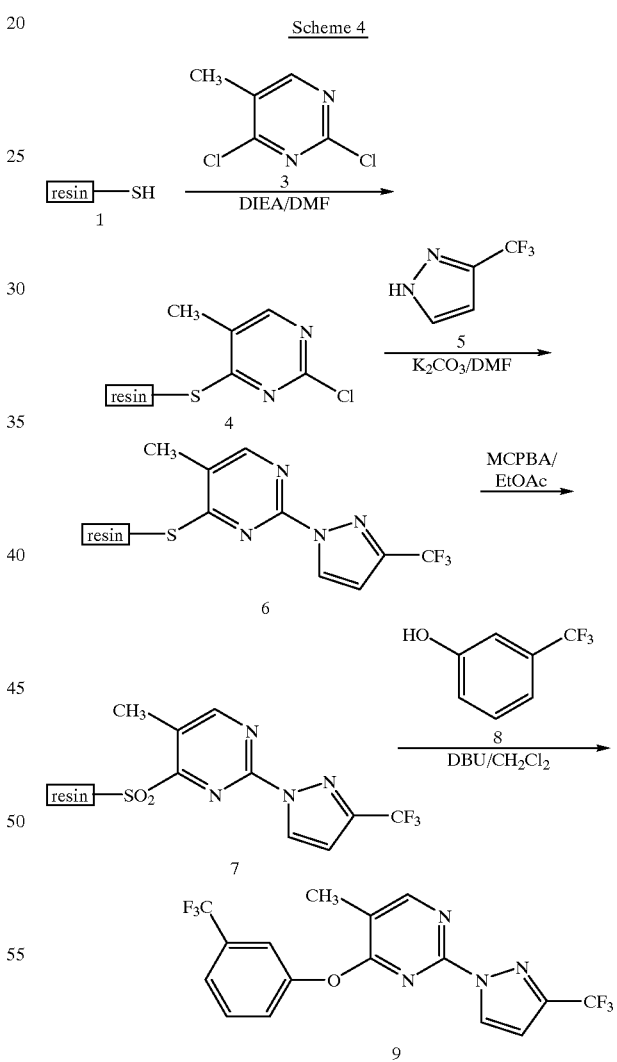

In solution phase synthesis, these resins can be used to simplify work up and purification procedures by acting as scavengers of electrophilic reagents and impurities. The use of scavenger resins in solution phase synthesis has been described by Kaldor et al., *Tetrahedron Lett.* 1996, 37, 7193–7196 and Booth and Hodges, *J. Am. Chem. Soc.* 1997, 119, 4882–886.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet. Mass spectra (MS) were obtained using atmospheric-pressure chemical ionization.

EXAMPLE 1

Preparation of 1% cross-linked γ-mercaptobutyramidomethyl functionalized poly(styrene-co-divinylbenzene) (Resin 1)

Beads of 1% cross-linked, aminomethylated poly (styrene-co-divinylbenzene) (100–200 mesh (75–150 μm), Advanced ChemTech, 1.2 meq N/g, 25.55 g) were suspended in a solution of γ-thiobutyrolactone (12 mL, approx. 4 eq. ) dissolved in toluene (300 mL). The mixture was stirred at 80° C. for 6 hours. Due to the progressive swelling observed over the course of the reaction, addition of further solvent was necessary to facilitate effective stirring. After cooling to room temperature, the resin product was filtered from the reaction mixture and washed with enough toluene to create a suspension of the solid material. The resin product was then washed successively with tetrahydrofuran and methanol (3 times) using volumes sufficient to create a suspension of the solid material. A final wash with diethyl ether and drying under vacuum yielded the desired Resin 1 as a free-flowing white powder. A ninhydrin test for free $NH_2$ groups was negative. IR (KBr): 1656, 2567 cm$^{-1}$; $^{13}$C NMR ($C_6D_6$): δ24.58, 30.12, 34.82, 41.25, 43.50, 128.00, 128.47, 128.24, 171.55.

To confirm loading by combustion analysis the 4-bromobenzyl-derivatized Resin 2 was prepared as follows:

Resin 1 (180 mg, 1.07 meq/g theoretical loading) was suspended in a solution of 4-bromobenzyl bromide (500 mg, approx. 10 eq.) dissolved in dichloromethane (3 mL). To this suspension was added N,N-diisopropylethylamine (0.35 mL, approx. 10 eq.) and the mixture shaken for 20 hours. The resin product was filtered from the reaction mixture and washed with enough dichloromethane to create a suspension of the solid material. The resin product was then washed successively with dichloromethane and methanol (3 times) using volumes sufficient to create a suspension of the solid material. A final wash with methanol and drying under vacuum yielded the bromobenzyl-derivatized Resin 2 as a free flowing white powder. Analysis: Calcd. (0.91 meq/g theoretical loading): N 1.27; S 2.92; Br 7.27. Found: N 1.18; S 2.90; Br 7.15.

A sample of Resin 1 stored in a clear glass vessel under normal atmosphere at room temperature for 8 months was treated with 4-bromobenzyl bromide in the manner described above to determine the stability of the free thiol groups over time. Analysis Found: N 1.14; S 2.86; Br 6.90. These analyses are considered accurate to ±0.4%.

EXAMPLE 2

Preparation of 2-(3 -trifluoromethylpyrazol-1-yl)-4-(3-trifluorctnethylphenoxy)-5-methylpyrimidine (9 in Scheme 4)

Step A

Resin 1 (27.72 g, 1.07 meq/g, 29.7 mmol) was suspended in a solution of 2,4-dichloro-5-methylpyrimidine (Aldrich, 11 g, approx. 2.25 eq.) dissolved in N,N-dimethylformamide (200 mL). The mixture was allowed to stir 5 minutes at room temperature to facilitate swelling of the resin. To the stirred mixture was added N,N-diisopropylethylamine (11.6 mL, approx. 2.25 eq.), and the reaction mixture was heated at 85° C. for 6 hours. Upon cooling to room temperature the resin product was filtered from the reaction mixture and washed with enough N,N-dimethylformamide to create a suspension of the solid material. The resin product was then washed successively with tetrahydrofuran and methanol (3 times) using volumes sufficient to create a suspension of the solid material. A final wash with methanol and drying under vacuum yielded the resin product (4 in Scheme 4). IR (KBr): 1656, 1209, 1169, 1104 cm$^{-1}$; $^{13}$C NMR ($C_6D_6$): δ14.39, 25.32, 29.31, 35.11, 155.95, 158.69, 171.83.

Step B

The product of Step A (9.0 g, 0.94 meq/g, 8.46 mmol) was suspended in a solution of 3-trifluoromethylpyrazole (5 g, approx. 4.3 eq.) dissolved in N,N-dimethylformamide (75 mL). The mixture was allowed to stir 5 minutes at room temperature to facilitate swelling of the resin. To the stirred mixture, potassium carbonate (6 g, approx. 5 eq.) was added and the reaction mixture was heated at 85–90° C. for approx. 24 hours. Upon cooling to room temperature the resin product was filtered from the reaction mixture and washed with enough N,N-dimethylformamide to create a suspension of the solid material. The resin product was then washed successively with tetrahydrofuran and water (3 times) using volumes sufficient to create a suspension of the solid material. A final wash with methanol and drying under vacuum yielded the resin product of Step B (6 in Scheme 4). IR (KBr): 1655, 1380, 1291, 1131 cm$^{-1}$; $^{13}$C NMR ($C_6D_6$): δ14.56, 25.73, 29.42, 35.16, 106.00, 153.27, 154.85, 171.23. Combustion analysis indicated approximately 80% conversion of chloropyrimidinyl-functionalized units in resin 4 to pyrazolylpyrimidinyl-functionalized units in resin 6. Analysis: Calcd. (100% conversion): F 4.90; N 6.02; S 2.76; Cl 0. Found: F 3.84; N 4.93; S 2.80; Cl 0.60.

Step C

The product of Step B (0.474 g, 0.6 meq/g, 0.28 mmol) was suspended in a dried ($MgSO_4$) solution of m-chloroperbenzoic acid (57–86%, 0.5 g, 5+ eq.) dissolved in ethyl acetate (5 mL). The mixture was shaken for 20 hours at room temperature. The resin product was filtered from the reaction mixture and washed repetitively with ethyl acetate (6×5 mL) and then dichloromethane (2×5 mL) to give the resin product of Step C (7 in Scheme 4). IR (KBr): 1657, 1390, 1315, 1143 cm$^{-1}$; $^{13}$C NMR ($C_6D_6$): δ14.02, 19.00, 33.72, 50.77, 106.57, 152.33, 163.89, 169.95.

Step D

The product of Step C (0.28 mmol) was treated with a solution of phenol (0.9 eq.) and 1,8-diazabicyclo[5.4.0] undec-7-ene (0.9 eq.) dissolved in dichloromethane (5 mL). The mixture was shaken for 20 hours at room temperature. The reaction mixture was filtered and the resin washed with dichloromethane (2 mL) and then ethyl acetate (3 mL). The combined organic filtrates were treated for 16 hours with Biorad AG 501-X8 mixed-bed ion exchange resin to remove any remaining phenol and 1,8-diazabicyclo[5.4.0]undec-7-ene. The combined organic filtrates were evaporated to dryness to yield 2-(3-trifluoromethylpyrazol-1-yl)-4-(3-trifluoromethylphenoxy)-5-methylpyrimidine (47 mg, 59%) (9 in Scheme 4). MS: 320.9 (M+1); $^{13}$H NMR (CDCl$_3$): δ2.40 (s, 3H), 6.61 (d, 1H), 7.44 (m, 1H), 7.56 (s, 1H), 7.61 (m, 2H), 8.07 (d, 1H), 8.54 (s, 1H).

By the procedures described herein together with methods known in the art, the following polymer resins of Table 1 can be prepared.

TABLE 1

Styrene polymers comprising

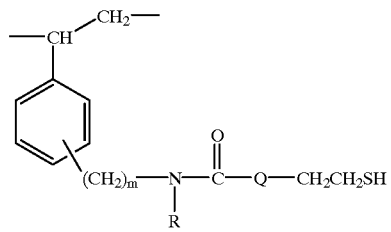

I

| Polymer | m | R | Q |
|---|---|---|---|
| A | 1 | H | —CH$_2$— |
| A | 1 | H | —CH$_2$CH$_2$— |
| A | 1 | H | —CH$_2$CH$_2$CH$_3$— |
| A | 1 | H | —CH(NHC(=O)CH$_3$)— |
| A | 1 | H | bond |
| A | 1 | CH$_3$ | —CH$_2$— |
| A | 1 | CH$_3$ | —CH$_2$CH$_2$— |
| A | 1 | CH$_3$ | —CH$_2$CH$_2$CH$_3$— |
| A | 1 | CH$_3$ | —CH(NHC(=O)CH$_3$)— |
| A | 1 | CH$_3$ | bond |
| A | 1 | CH$_2$CH$_3$ | —CH$_2$— |
| A | 1 | CH$_2$CH$_3$ | —CH$_2$CH$_2$— |
| A | 1 | CH$_2$CH$_3$ | —CH$_2$CH$_2$CH$_3$— |
| A | 1 | CH$_2$CH$_3$ | —CH(NHC(=O)CH$_3$)— |
| A | 1 | CH$_2$CH$_3$ | bond |
| A | 1 | CH$_2$CH$_2$CH$_3$ | —CH$_2$— |
| A | 1 | CH$_2$CH$_2$CH$_3$ | —CH$_2$CH$_2$— |
| A | 1 | CH$_2$CH$_2$CH$_3$ | —CH$_2$CH$_2$CH$_3$— |
| A | 1 | CH$_2$CH$_2$CH$_3$ | —CH(NHC(=O)CH$_3$)— |
| A | 1 | CH$_2$CH$_2$CH$_3$ | bond |
| A | 2 | H | —CH$_2$— |
| A | 2 | H | —CH$_2$CH$_2$— |
| A | 2 | H | —CH$_2$CH$_2$CH$_3$— |
| A | 2 | H | —CH(NHC(=O)CH$_3$)— |
| A | 2 | H | bond |
| A | 2 | CH$_3$ | —CH$_2$— |
| A | 2 | CH$_3$ | —CH$_2$CH$_2$— |
| A | 2 | CH$_3$ | —CH$_2$CH$_2$CH$_3$— |
| A | 2 | CH$_3$ | —CH(NHC(=O)CH$_3$)— |
| A | 2 | CH$_3$ | bond |
| A | 2 | CH$_2$CH$_3$ | —CH$_2$— |
| A | 2 | CH$_2$CH$_3$ | —CH$_2$CH$_2$— |
| A | 2 | CH$_2$CH$_3$ | —CH$_2$CH$_2$CH$_3$— |
| A | 2 | CH$_2$CH$_3$ | —CH(NHC(=O)CH$_3$)— |
| A | 2 | CH$_2$CH$_3$ | bond |
| A | 2 | CH$_2$CH$_2$CH$_3$ | —CH$_2$— |
| A | 2 | CH$_2$CH$_2$CH$_3$ | —CH$_2$CH$_2$— |
| A | 2 | CH$_2$CH$_2$CH$_3$ | —CH$_2$CH$_2$CH$_3$— |
| A | 2 | CH$_2$CH$_2$CH$_3$ | —CH(NHC(=O)CH$_3$)— |
| A | 2 | CH$_2$CH$_2$CH$_3$ | bond |
| A | 3 | H | —CH$_2$— |
| A | 3 | H | —CH$_2$CH$_2$— |
| A | 3 | H | —CH$_2$CH$_2$CH$_3$— |
| A | 3 | H | —CH(NHC(=O)CH$_3$)— |
| A | 3 | H | bond |
| A | 3 | CH$_3$ | —CH$_2$— |
| A | 3 | CH$_3$ | —CH$_2$CH$_2$— |
| A | 3 | CH$_3$ | —CH$_2$CH$_2$CH$_3$— |
| A | 3 | CH$_3$ | —CH(NHC(=O)CH$_3$)— |
| A | 3 | CH$_3$ | bond |
| A | 3 | CH$_2$CH$_3$ | —CH$_2$— |
| A | 3 | CH$_2$CH$_3$ | —CH$_2$CH$_2$— |

TABLE 1-continued

Styrene polymers comprising

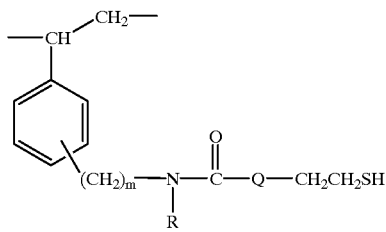

I

| Polymer | m | R | Q |
|---|---|---|---|
| A | 3 | CH$_2$CH$_3$ | —CH$_2$CH$_2$CH$_3$— |
| A | 3 | CH$_2$CH$_3$ | —CH(NHC(=O)CH$_3$)— |
| A | 3 | CH$_2$CH$_3$ | bond |
| A | 3 | CH$_2$CH$_2$CH$_3$ | —CH$_2$— |
| A | 3 | CH$_2$CH$_2$CH$_3$ | —CH$_2$CH$_2$— |
| A | 3 | CH$_2$CH$_2$CH$_3$ | —CH$_2$CH$_2$CH$_3$— |
| A | 3 | CH$_2$CH$_2$CH$_3$ | —CH(NHC(=O)CH$_3$)— |
| A | 3 | CH$_2$CH$_2$CH$_3$ | bond |
| B | 1 | H | —CH$_2$— |
| B | 1 | H | —CH(NHC(=O)CH$_3$)— |
| B | 1 | CH$_3$ | —CH$_2$— |
| B | 1 | CH$_3$ | —CH(NHC(=O)CH$_3$)— |
| C | 1 | H | —CH$_2$— |
| C | 1 | H | —CH(NHC(=O)CH$_3$)— |
| C | 1 | CH$_3$ | —CH$_2$— |
| C | 1 | CH$_3$ | —CH(NHC(=O)CH$_3$)— |
| D | 1 | H | —CH$_2$— |
| D | 1 | H | —CH(NHC(=O)CH$_3$)— |
| D | 1 | CH$_3$ | —CH$_2$— |
| D | 1 | CH$_3$ | —CH(NHC(=O)CH$_3$)— |
| E | 1 | H | —CH$_2$— |
| E | 1 | H | —CH(NHC(=O)CH$_3$)— |
| E | 1 | CH$_3$ | —CH$_2$— |
| E | 1 | CH$_3$ | —CH(NHC(=O)CH$_3$)— |
| F | 1 | H | —CH$_2$— |
| F | 1 | H | —CH(NHC(=O)CH$_3$)— |
| F | 1 | CH$_3$ | —CH$_2$— |
| F | 1 | CH$_3$ | —CH(NHC(=O)CH$_3$)— |

A is 1% cross-linked poly(styrene-co-divinylbenzene).
B is 2% cross-linked poly(styrene-co-divinylbenzene).
C is 4% cross-linked poly(styrene-co-divinylbenzene).
D is 8% cross-linked poly(styrene-co-divinylbenzene).
E is considered an equivalent of Chiron Technologies' polystyrene grafted polyethylene SynPhase ™ crowns.
F is considered an equivalent of Irori Quantum Microchemistry's polystyrene grafted polypropylene MicroTube ™ reactors.

What is claimed is:

1. A polymer comprising mercaptoalkylamide-functionalized styrene units of Formula I

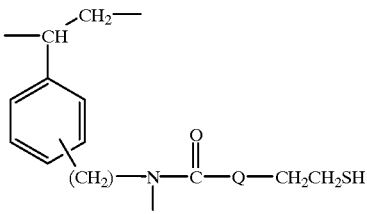

I wherein

R is H or C$_1$–C$_3$ alkyl; and

Q is —CH$_2$— or —CH(NHC(=O)CH$_3$)—.

2. A polymer of claim 1 wherein R is H, and Q is —CH$_2$—.

3. A polymer of claim 2 consisting essentially of a polystyrene backbone which is cross-linked with about 0.5 to 20% by weight divinylbenzene units.

4. A polymer of claim 1 consisting essentially of a polystyrene backbone which is cross-linked with about 0.8 to 8% by weight divinylbenzene units.

5. A polymer of claim 4 which is cross-linked with about 1 to 2% by weight divinylbenzene units.

6. A bead comprising the polymer of claim 1.

7. A process for preparing the polymer of claim 1, the process comprising the sequential steps of:

(a) contacting a polymer comprising aminoalkyl-functionalized styrene units of Formula II

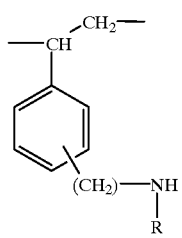

with a solvent to swell said polymer; and (b) reacting said polymer with a thiolactone of Formula III

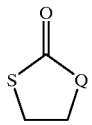

at a temperature of 0 to 120° C.;

wherein R and Q are as described in claim 1.

8. A process for producing a product compound from a modifiable substrate precursor that bonds to the sulfur atom of a mercaptan group, comprising:

(a) reacting the precursor with a polymer comprising mercaptoalkylamide-functionalized styrene units of Formula I of claim 1 to bind the precursor to the sulfur of one of said functionalized styrene units;

(b) modifying the bound precursor;

(c) oxidizing the sulfur to which the modified precursor is bound; and (d) cleaving the modified precursor by nucleophilic displacement to produce the product compound.

9. A polymer comprising mercaptoalkylamide-functionalized styrene units of Formula I

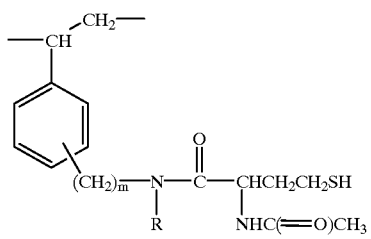

wherein m is an integer from 1 to 3; and

R is H or $C_1$–$C_3$ alkyl.

10. A polymer of claim 9 wherein m is 1 and R is H.

11. A polymer of claim 10 consisting essentially of a polystyrene backbone which is cross-linked with about 0.5 to 20% by weight divinylbenzene units.

12. A bead comprising the polymer of claim 9.

13. A process for preparing the polymer of claim 9, the process comprising the sequential steps of:

(a) contacting a polymer comprising aminoalkyl-functionalized styrene units of Formula II

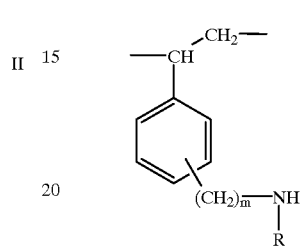

with a solvent to swell said polymer; and (b) reacting said polymer with a thiolactone of Formula III

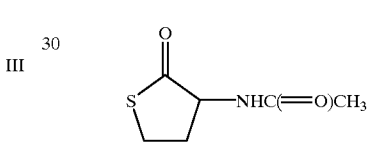

at a temperature of 0 to 120° C.;

wherein m and R are as described in claim 1.

14. A process for producing a product compound from a modifiable substrate precursor that bonds to the sulfur atom of a mercaptan group, comprising:

(a) reacting the precursor with a polymer comprising mercaptoalkylamide-functionalized styrene units of Formula I of claim 9 to bind the precursor to the sulfur of one of said functionalized styrene units;

(b) modifying the bound precursor;

(c) oxidizing the sulfur to which the modified precursor is bound; and (d) cleaving the modified precursor by nucleophilic displacement to produce the product compound.

15. A polymer comprising mercaptoalkylamide-functionalized styrene units of Formula I

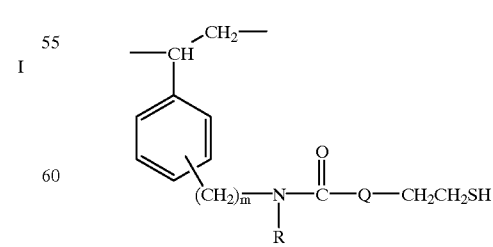

wherein m is an integer from 1 to 3;

R is $C_1$–$C_3$ alkyl; and

Q is a bond, —CH₂—, —CH₂CH₂—, —CH₂CH₂CH₂— or

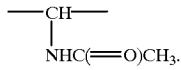

16. A polymer of claim 15 wherein m is 1 and Q is —CH₂—.

17. A polymer of claim 15 consisting essentially of a polystyrene backbone which is cross-linked with about 0.5 to 20% by weight divinylbenzene units.

18. A bead comprising the polymer of claim 15.

19. A process for preparing the polymer of claim 15, the process comprising the sequential steps of:

(a) contacting a polymer comprising aminoalkyl-functionalized styrene units of Formula II

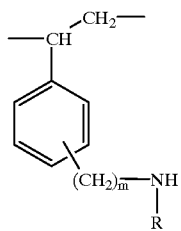

with a solvent to swell said polymer; and (b) reacting said polymer with a thiolactone of Formula III

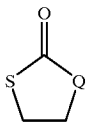

at a temperature of 0 to 120° C.;

wherein m, R and Q are as described in claim 15.

20. A process for producing a product compound from a modifiable substrate precursor that bonds to the sulfur atom of a mercaptan groups comprising:

(a) reacting the precursor with a polymer comprising mercaptoalkylamide-functionialized styrene units of Formula I of claim 15 to bind the precursor to the sulfur of one of said functionalized styrene units;

(b) modifying the bound precursor;

(c) oxidizing the sulfur to which the modified precursor is bound; and (d) cleaving the modified precursor by nucleophilic displacement to produce the product compound.

* * * * *